United States Patent [19]

Hankel et al.

[11] Patent Number: 5,566,570

[45] Date of Patent: Oct. 22, 1996

[54] METHOD AND APPARATUS FOR EVALUATING FOLD ENDURANCE AND SURFACE ADHESION OF SHEET MATERIALS

[75] Inventors: Steven G. Hankel, Blue Mounds; Dennis E. Gunderson, Madison; C. Timothy Scott, Mt. Horeb; Roland L. Gleisner, Jr., Jefferson, all of Wis.

[73] Assignee: Director, Bureau of Engraving and Printing, Department of the Treasury

[21] Appl. No.: 278,586

[22] Filed: Jul. 21, 1994

[51] Int. Cl.[6] ................................................ B21D 7/04
[52] U.S. Cl. ........................... 73/159; 73/150 R; 73/849
[58] Field of Search ............................ 73/159, 150 A, 73/150 R, 808, 838, 849, 851

[56] References Cited

U.S. PATENT DOCUMENTS

| | | | |
|---|---|---|---|
| 3,057,191 | 10/1962 | Holloway | 73/849 |
| 3,776,029 | 12/1973 | McKee | 73/88 R |
| 4,578,052 | 3/1986 | Engel et al. | 73/159 X |
| 4,819,489 | 4/1989 | Nelson et al. | 73/150 A X |
| 4,938,071 | 7/1990 | Kobayashi et al. | 73/849 |
| 4,942,769 | 7/1990 | Jarvinen et al. | 73/82.1 |
| 5,182,722 | 1/1993 | Hain | 364/551 |
| 5,199,305 | 4/1993 | Smith et al. | 73/150 A X |
| 5,201,424 | 4/1993 | Hain | 209/534 |
| 5,419,202 | 5/1995 | Howard et al. | 73/849 |

OTHER PUBLICATIONS

D 2097–69 Standard Method of Flex Testing of Finish on Upholstery Leather.

*Primary Examiner*—Richard Chilcot
*Assistant Examiner*—Elizabeth L. Dougherty
*Attorney, Agent, or Firm*—Janet I. Stockhausen; M. Howard Silverstein; John D. Fado

[57] ABSTRACT

An apparatus and method uses vacuum restraint, or other pressure differential, to hold the ends of a sheet specimen to two opposing surfaces, thereby creating a fold in the specimen. As the opposing surfaces cycle along a parallel axis in opposite directions, the fold repeatedly rolls through a specific region of the specimen. The spacing between the opposing surfaces can be adjusted to increase or to decrease the radius of the fold. The velocity of the fold and the number cycles also can be controlled precisely. After repeated movement of the fold, the adhesion of surface treatments, coatings or printing on the specimen substrate begins to break down. Additionally, the integrity of the substrate itself may begin to deteriorate, if it is susceptible to deterioration and to varying degrees depending upon the susceptibility. The extent to which the specimen coating is degraded and substrate integrity reduced is a function of spacing, fold velocity and number of cycles.

17 Claims, 5 Drawing Sheets

METHOD AND APPARATUS FOR EVALUATING FOLD ENDURANCE AND SURFACE ADHESION OF SHEET MATERIALS

Cross-references to related applications, if any: None.

BACKGROUND OF THE INVENTION

1. Field of the Invention

The present invention relates generally to testing the endurance of flexible sheets and the adhesion of surface treatments, coatings, and print to the surface of such sheets, as well as the bonding of multilayer sheets. More specifically, the present invention relates to the creation of a small radius fold in a sheet specimen and methods of restraining the specimen with a pressure differential. The fold can be shifted progressively across the sheet in a controlled manner by manipulating the sheet specimen.

2. Description of Related Art

A number of fold endurance testers have been developed in the past. Some of these testers were capable of producing a sharp fold at one location with no sliding contact with the specimen. These devices merely folded and unfolded the sheet material repeatedly at a single line. However, a repeated fold at one location is relatively ineffective in the evaluation of printing durability or adhesion of other surface treatments. A moving line of fold or flexure is necessary for the efficient testing of sheet specimens.

There are also devices which can cause a fold line to progress and recede over the surface of a specimen by means of rubbing or rolling contact with the specimen at the line of fold. If the line of fold is created and/or controlled by a roller, the minimum radius of the fold is severely limited. Since flexural stress in a folded specimen is proportional to the inverse of the fold radius (i.e., stress can be increased significantly by decreasing the radius of the fold), a roller severely limits a flexural stress which may be applied to the specimen.

Smaller bend radii at the fold line are made possible by using a sliding contact at the inner radius on some devices. However, this approach limits the speed at which the test may be conducted, because of the heat generated by friction at the fold line. Moreover, the stress on the specimen in rubbing contact is an indefinable combination of cyclic flexure, shear at the surface, abrasion and wear. Thus, failure modes are inextricably mixed.

The present invention is for a method and apparatus for testing the flexural durability and structural integrity of sheet materials and the adhesion and durability of surface treatments (such as printing and/or coatings) which permits testing without the use of rollers or rubbing surface contact, and permits testing with bend radii approaching zero, overcomes the shortcomings of earlier devices and represents a significant advancement in the art. In those applications where flexural endurance is used to determine the adhesion of printing, coatings, or other surface treatments, rubbing and/or sliding contact of the surface against itself is unacceptable.

one immediate application of the present invention is in evaluating the print durability of currency notes. In this application, the present invention will replace a device that was intended only for testing of the structural integrity of the material being tested. It was never intended to test for the adhesion or durability of surface treatments. That device was labor intensive, time consuming and sensitive to operator manipulation. The present invention will reveal process defects not otherwise apparent by current methods.

The inventors are unaware of any method or apparatus which produces a moving, 180° fold line of extremely small inside radius in a sheet specimen. No mechanically clamped specimens are required in the process. The inventors believe that the present invention is likely to fulfill a similar need within specialized segments of the paper and plastic film industries. The invention represents a breakthrough in timely durability testing of currency, removing a barrier to the development of effective quality control that has existed for many years. As a result, it is likely that the present invention has potential for widespread use. The durability testing assists also in determining the structural integrity of the materials used in producing the sheets being tested as specimens.

OBJECTS AND SUMMARY OF THE INVENTION

It is a first principal object of the present invention to provide a method and apparatus for testing the flexural durability of a sheet material specimen by moving a 180° fold across the sheet material repeatedly without sliding or rolling contact against the face of the specimen at the inside radius of the fold.

It is a second principal object of the present invention to provide a method and apparatus for testing the flexural durability of a sheet material specimen which also can test the durability of the bond between layers of a composite sheet material and the adhesion durability of printing, coatings and other surface treatments on the surface of the specimen.

It is a different object of the present invention to provide a method and apparatus for testing the flexural durability of a sheet material specimen which can achieve very small bend radii in the specimen.

It is one other object of the present invention to provide a method and apparatus for testing the flexural durability of a sheet material specimen which can be used to evaluate the print durability of currency notes.

How these and other objects of the present invention are accomplished will be explained in the detailed description of the preferred and alternate embodiments of the invention in connection with the FIGURES. Generally, however, the objects of the invention are accomplished in an apparatus and method using vacuum suction to hold the ends of a sheet specimen to two opposing surfaces, thereby creating a fold in the specimen. As the opposing surfaces move in opposite directions, the fold in the specimen sheet continuously shifts. The opposing surfaces can be moved back and forth repeatedly, creating a moving fold in the specimen. The spacing between the opposing surfaces can be adjusted to increase or to decrease the radius of the fold. After repeated movement of the fold, the adhesion of surface treatments, coatings or printing on the surface of the specimen begins to break down. Additionally, the substrate itself may begin to deteriorate after repeated folding. The extent to which the surface coating is degraded and/or substrate integrity reduced can be measured in subsequent tests.

Other variations, modifications, applications, advantages and ways in which the objects are accomplished will become apparent to those presently of ordinary skill in the art after reviewing the specification and are deemed to fall within the scope of the present invention if they fall within the scope of the claims which follow the description of the preferred and alternate embodiments.

DETAILED DESCRIPTION OF THE DRAWINGS

In the FIGURES, like reference numerals refer to like components.

DESCRIPTION OF THE PREFERRED EMBODIMENT

The present invention relates generally to the testing of flexible sheets of material. Such sheets are tested to determine the structural integrity of the materials from which they are made. One such intended material includes cellulose, cellulosic materials, and combinations of cellulosic and other materials. The cellulosic materials can include wood pulp, cotton, flax, hemp, jute, ramie, and regenerated unsubstituted wood celluloses such as rayon. Combinations of said cellulosics and combinations of said cellulosics with other fibers such as polyesters, silk, nylons, plastics, acrylics, and the like also can be tested.

In cases where printing, coating or other surface treatments are applied, the present invention also permits the testing of ink adhesion and the adhesion and durability of other surface coatings and treatments. The invention is generally shown in FIGS. 1–6.

Figure 1:
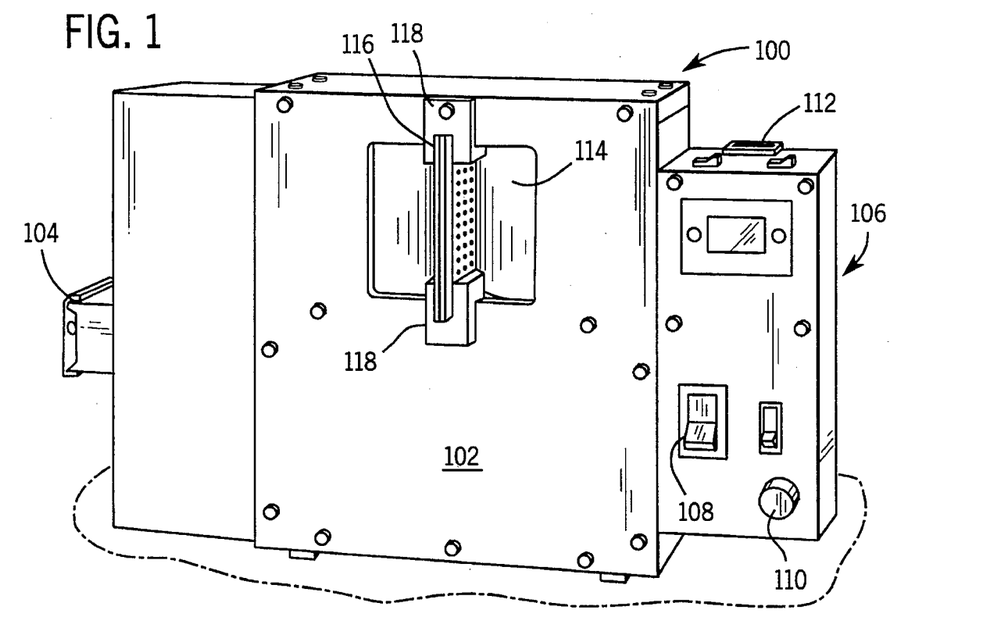
FIG. 1 is an external perspective view of the first alternate embodiment of the present invention.

FIG. 1 illustrates an external view of one embodiment of the present invention. The external controls and features of the present invention are a matter of design choice. The view in FIG. 1 is provided for illustrative purposes. The testing device 100 includes an external frame 102 and a power source 104. A control mechanism 106 is mounted to external frame 102.

Control panel 106 includes an on/off switch 108 and a fuse 110. Controls for separation spacing, cycle count setting and resetting, vacuum control and fold velocity may also be provided. A cycle display 112 may also be provided to display the number of cycles completed. Device 100 includes a front entry aperture 114 having a shim 116 to assist in inserting a sheet for testing. Shim 116 slides in guides 118.

It has been found that introduction of the specimen into the testing device 100 can be simplified by folding the specimen over a thin sheet of metal shimstock and using the shimstock to insert the specimen into a space between perforated surfaces. Tapering of the entry aperture 114 further assists in this phase of the testing. Other guides can be used to permit easier entry and proper positioning of the shimstock insertion tool.

Figure 2A:
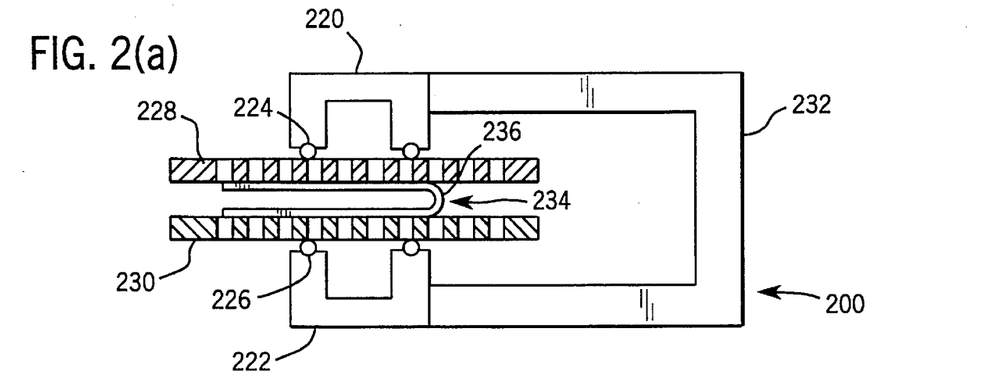
FIG. 2A is a schematic side view of the preferred embodiment of the present invention in a first operational position.
Figure 2B:
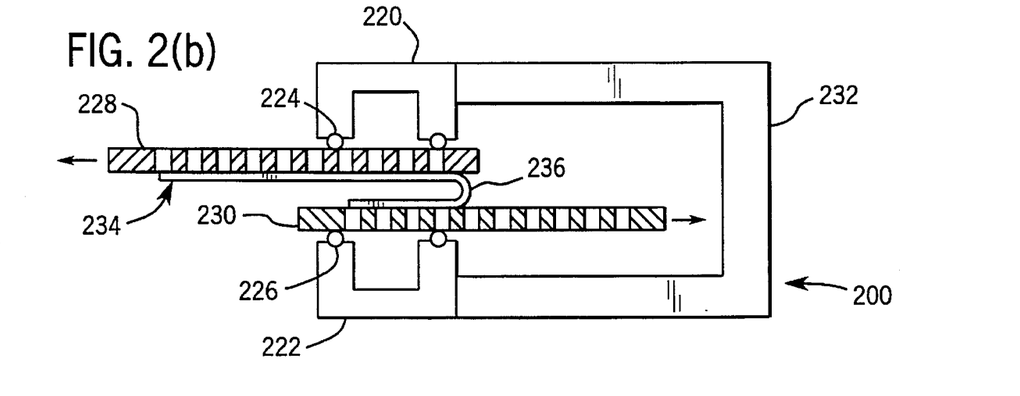
FIG. 2B is a schematic side view of the preferred embodiment of the present invention in a second operational position.
Figure 2C:
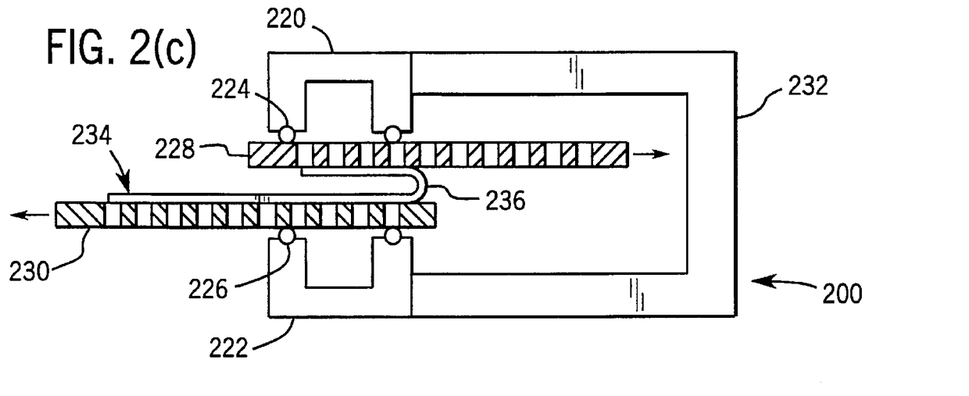
FIG. 2C is a schematic side view of the preferred embodiment of the present invention in a third operational position.

FIGS. 2A–2C show the preferred embodiment of the present invention in a device 100. FIGS. 2A–2C illustrate the most basic embodiment of the present invention. Upper and lower stationary vacuum boxes 220 and 222, respectively, have vacuum chambers and seals 224 and 226, respectively. Seals 224 and 226 are effective about the entire perimeter of each vacuum box, preventing air from being drawn into the vacuum boxes at the upper surface of porous plate 228 and the lower surface of porous plate 230.

An elevated pressure in the cavity in which the specimen 234 is held can also be used to create a pressure differential to hold specimens in place on the plates 228 and 230 instead of a vacuum. Alternatively, a combination of elevated pressure and vacuum also may be used. Electrostatic force also can hold a specimen in place on the translating plates. Appropriate electrostatic forces can be generated in conventional ways (e.g., in the same manner as that used with the plotting surface of x-ray recorder instruments and to motivate film-to-core attraction during automatic roll changes in a web-handling apparatus).

Porous plates 228 and 230 are supported by a conventional slide means 232, which allows the plates 228 and 230 to translate in directions opposite one another. The distance between plates 228 and 230 is controlled precisely by slide means 232, which is of conventional design. Plates 228 and 230 can be hinged to permit easy access to the space therebetween for insertion of a specimen and for cleaning and maintenance.

The porosity of plates 228 and 230 is directional, so that air may pass freely through the thickness of the plate, while maintaining a pressure differential on the specimen 234. Plates 228 and 230 may be designed to be easily removable from the device, so that a folded specimen could be placed in the plates, and the plates inserted into the device. At the end of the test cycle, the plates would be removed from the device, and the test specimen retrieved. Such a configuration would facilitate periodic maintenance likely to be necessary to remove ink or other debris lost by the test specimen.

FIG. 2A shows the edge view of a specimen of sheet material 234 folded in half and positioned so that the line of fold is directly below the sliding seals 224 and at right angles to the direction of motion of the porous plates 228 and 230. The specimen 234 need not be confined entirely to the space between the plates 228 and 230. The corners, or "tails" of the specimen 234 can overhang the ends of the plates 228 and 230 to facilitate removal of the specimen after testing.

It may also be desirable to secure the tails of the specimen in some manner. Several methods of accomplishing this are acceptable. A constant vacuum can be applied to the ends of the specimen. The tail of the specimen might also be clamped mechanically by conventional means to the porous surfaces. One such configuration is shown in FIG. 2E. A clamp 242 holds one end of the specimen 234 to plate 228, while a second clamp 244 holds the other end of specimen 234 to plate 230. A clamp used in this configuration must be of a low profile so that it will not interfere with the very limited space between the plates 228 and 230 (or the nip between rollers or drums). Such mechanical means can be used to augment holding of the specimen by a pressure differential.

The reduced pressure in the vacuum boxes 220 and 222 is communicated to the specimen 234 through the porous plates 228 and 230. The specimen 234 is thus drawn to the plates 228 and 230 and held firmly in contact with the surface of each plate. When the plates 228 and 230 are then moved, relative to one another, the line of fold in the specimen 234 rolls along the surface of the specimen 234, but remains stationary with respect to vacuum boxes 220 and 222. Positive and negative motions of equal length by the two perforated plates (or other directionally porous surfaces) cause the line of fold to be stationary within the apparatus and the rolling fold action to be repeated in a specified region of the specimen. If the motion of each of the two surfaces is designed to be independent of the other, the device can be programmed to perform tests in more than one area of the specimen.

Figure 2D:
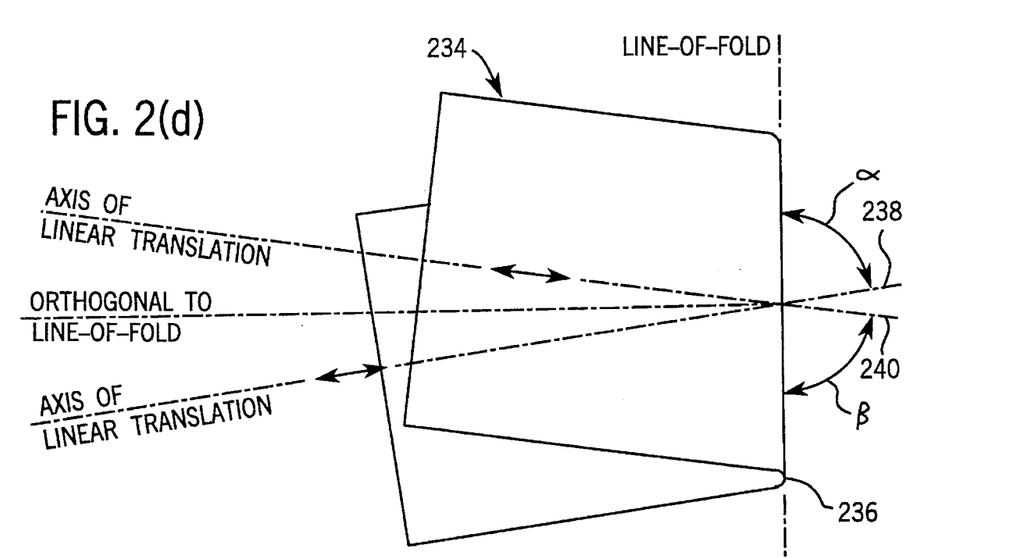
FIG. 2D is a plan view of a sheet specimen folded for testing by the present invention using an off-axis line of fold.
Figure 2E:
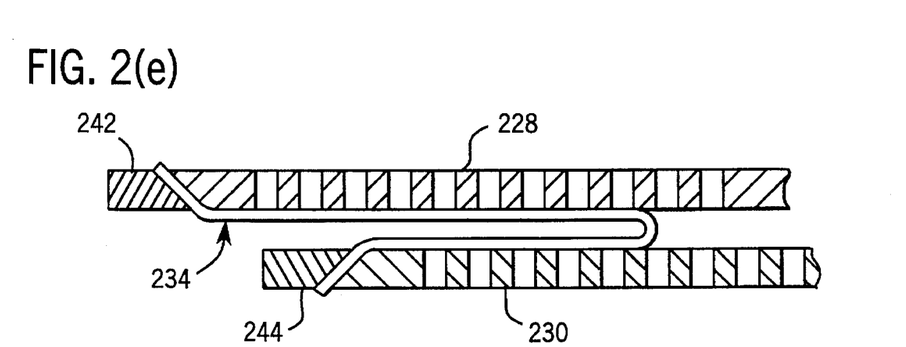
FIG. 2E is a schematic side view of a sheet secured for testing by mechanical clamp means in an operational position.

FIG. 2D illustrates one other variation on use of the invention. Linear translation of the perforated plates 228 and 230 may not necessarily be along axes orthogonal to the line of fold 236. In fact, the effect on the specimen 234 could be made more rigorous if the line of fold 236 is oriented at various angles to the axis of translation. FIG. 2D illustrates this feature. Angles $\alpha$ and $\beta$, which are measured from the line of fold 236 to the axis of linear translation (here indicated by lines 238 and 240) need not be 90°, but must be equal in magnitude.

For the line of fold 236 to remain stationary relative to the apparatus 200, the travel of the linearly translating perforated plates 228 and 230 must be equal in magnitude and opposite to one another relative to one another in direction. As is apparent, there is no limit to the magnitude of angles $\alpha$ and $\beta$. If these angles are increased continuously, without accompanying linear translation, a radial line of fold pattern can be produced on the specimen 234.

The pressures holding the specimen 234 in contact with plates 228 and 230 are always located in the area immediately adjacent to the fold 236. This is the location where restraint is required to allow a fold to roll through a specific region of the specimen 234. This feature is further illustrated in FIGS. 2B and 2C, in which plates 228 and 230 have been moved in opposite directions relative to one another. At no time does the specimen 234 slide with respect to either plate 228, 230. The surface of plates 228 and 230 (or any other configuration used to hold the specimen) can be modified to enhance the restraint provided by differential pressure. Possible modifications include high friction or abrasive coating, or an array of needle points which actually pierce the specimen in an area remote from the testing area to prevent in-plane slipping. Small "curbs" on the engaging surfaces of the plates may also be used to prevent slippage of the specimen during testing.

The spacing between surfaces which determines the radius of the fold can be changed to account for different material thicknesses or for changes in the degree of severity desired. So long as the space between the plates 228, 230 is greater than twice the thickness of the specimen 234, there is no contact between inner faces of the specimen 234. The inside curvature can be very small, approaching zero, if desired. It is possible, and may be desirable, to initiate testing at a wide spacing, and then to change the spacing of the surfaces as testing progresses. This method likely will find particular application with testing of strong or stiff materials. The exercise process could begin gently at a large spacing, and become increasingly more severe as the specimen loses strength and stiffness.

Figure 2F:
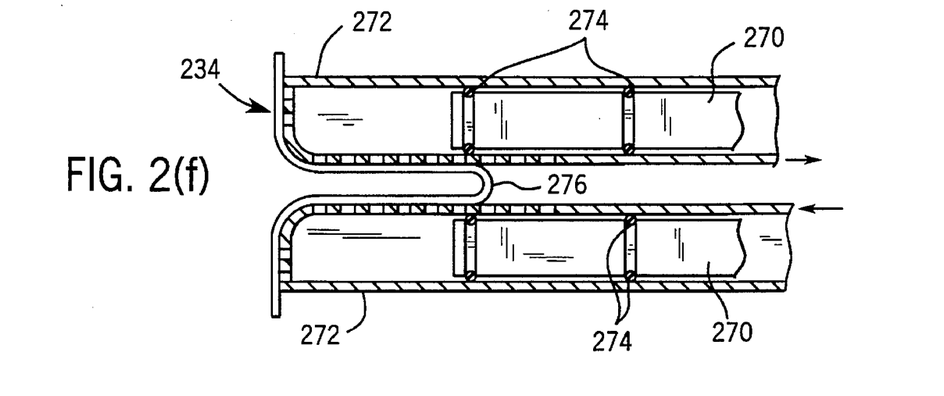
FIG. 2F is a schematic side view of a sheet secured for testing by a reciprocating piston and cylinder means in an operational position.
Figure 2G:
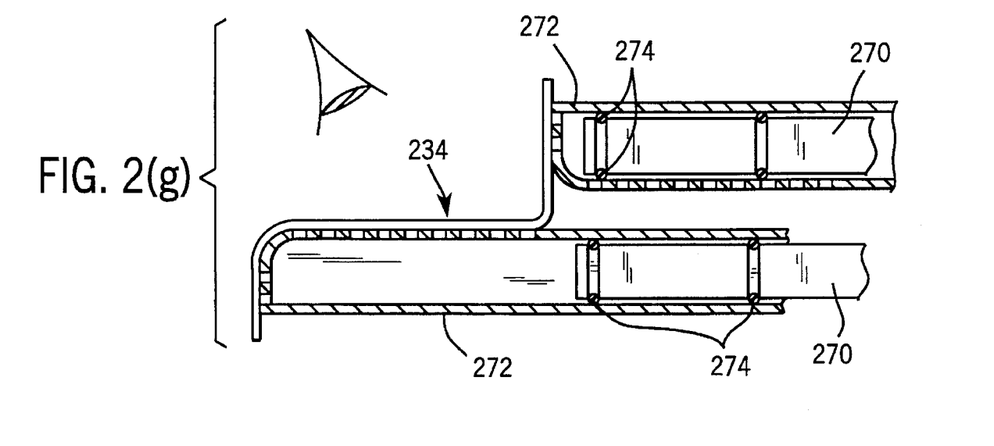
FIG. 2G is a schematic side view of a sheet secured for testing by a reciprocating piston and cylinder means in an operational position permitting visual or optical inspection of the specimen during testing.

Several alternate embodiments also are contemplated with the present invention. FIG. 2F shows another parallel plate configuration in which rectangular pistons 270 have fixed positions and the perforated outer cylinders 272 oscillate in opposing directions to maintain a fold line 276. 0-rings 274 maintain a vacuum in preselected sections of the cylinders 272. By including perforations on the noses of cylinders 272, the specimen may be clamped to the cylinder noses, as seen in FIG. 2G. This embodiment permits in-place visual or optical inspection of the specimen before and after testing.

Figure 3:
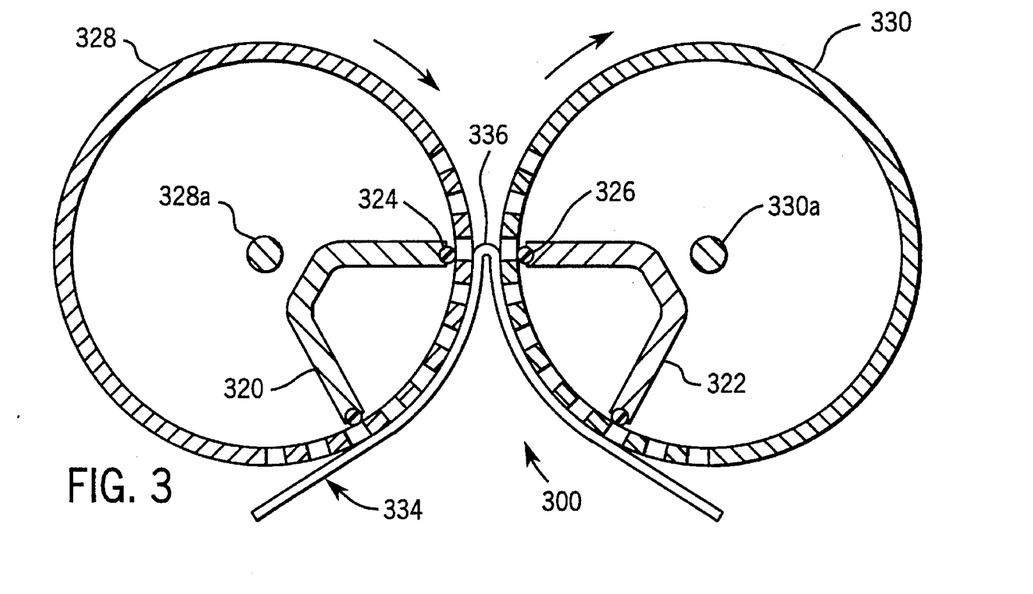
FIG. 3 is a schematic side view of a first alternate embodiment of the present invention in an operational position.

FIG. 3 shows a device 300 in which the porous plates 228 and 230 of FIGS. 2A–2C have been replaced by porous drums 328 and 330. Drums 328 and 330 are capable of restricted rotation about their axes 328a and 330a. Stationary vacuum boxes 320 and 322 are fixedly positioned within drums 328 and 330, respectively. Seals 324 and 326 on the vacuum boxes prevent air from being drawn into the vacuum box past the inner diameter of each drum. Folded specimen 334 is held to the exterior surface of the drums 328 and 330 by the vacuum communicated to those drums through the porous walls of each drum.

Drums 328 and 330 are porous in a radial direction only. As is apparent from FIG. 3, if drums 328 and 330 are rotated in equal increments in the same direction (e.g., clockwise), the line of fold 336 will roll along the specimen 334 while the line of fold 336 itself remains fixed relative to the nip between the drums 328 and 330. This alternate embodiment shown in FIG. 3 is functionally equivalent to that of FIGS. 2A–2C. As is apparent from the geometry of the dual drum design of FIG. 3, as the drums become larger in size, this alternate embodiment becomes virtually identical to the preferred embodiment using a dual porous plate configuration.

Another alternate embodiment is shown in FIGS. 4A–4E. Once again, this embodiment is functionally similar to that of FIGS. 2A–2C, except that the porous plates 228 and 230 have been replaced by two perforated continuous belts 428 and 430, which run over parallel rollers 438 and 440, respectively. With belts 428 and 430 moving in a direction generally indicated by arrows 442 in FIG. 4A, the folded specimen 434 is fed into the space between belts 428 and 430 until the line of fold 436 reaches a desired position at the seal line of the vacuum boxes 420 and 422.

Figure 4A:
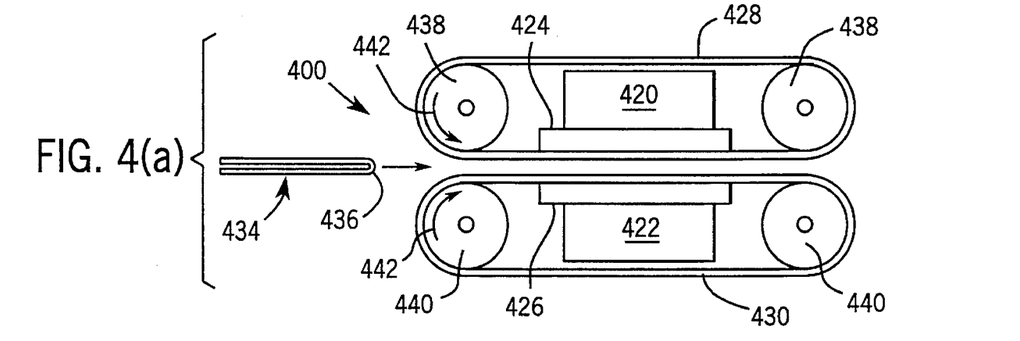
FIG. 4A is a is a schematic side view of a second alternate embodiment of the present invention with a folded sheet specimen prepared for insertion and testing.
Figure 4B:
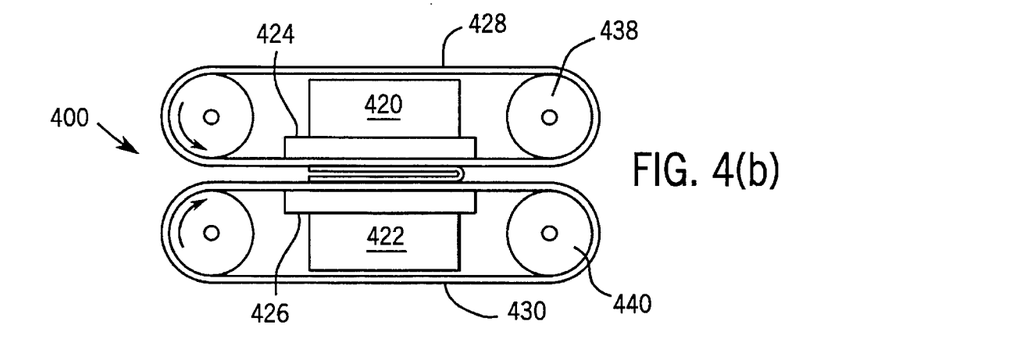
FIG. 4B is a is a schematic side view of the second alternate embodiment of the present invention with a folded sheet specimen inserted for testing.

Seal boxes 424 and 426 define an area on belts 428 and 430, respectively, where a vacuum is applied through the directional porosity of the belts to hold a specimen 434 in a desired orientation and to move the specimen 434 in a preselected manner, while maintaining the line of fold 436 in its preselected position. FIG. 4B illustrates the line of fold being in a preselected desired position relative to vacuum boxes 420 and 422 and seal boxes 424 and 426.

Figure 4C:
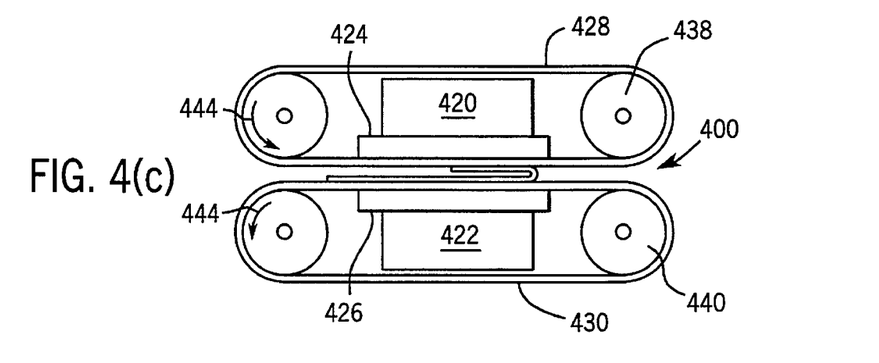
FIG. 4C is a is a schematic side view of the second alternate embodiment of the present invention with a folded sheet specimen inserted for testing wherein the fold in the sheet specimen has been translated a preselected distance.
Figure 4D:
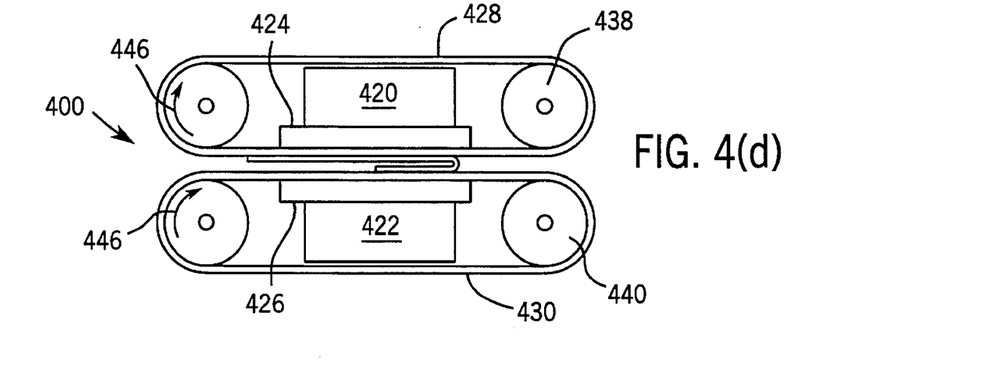
FIG. 4D is a is a schematic side view of the second alternate embodiment of the present invention with a folded sheet specimen inserted for testing wherein the fold in the sheet specimen has again been translated a preselected distance.

With belts 428 and 430 moving in the direction generally indicated b? arrows 444, as seen in FIG. 4C, and arrows 446, as seen in FIG. 4D, it can be seen that the line of fold 436 will translate back and forth across the face of the specimen 434 in a manner similar to that illustrated in FIGS. 2B and 2C with respect to the preferred embodiment.

Figure 4E:
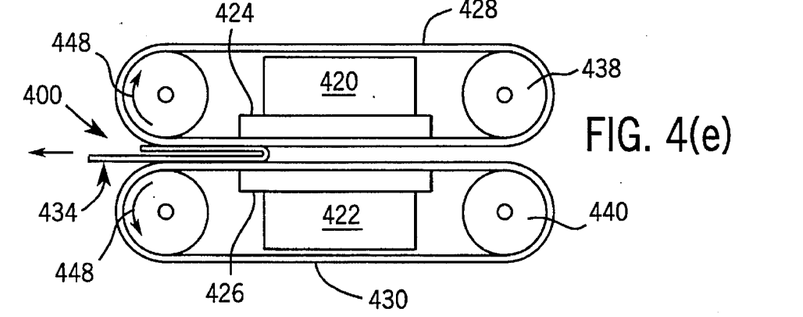
FIG. 4E is a is a schematic side view of the second alternate embodiment of the present invention with a folded sheet specimen being ejected after testing.

When a sufficient number of rolling fold cycles have been completed, the belts 428 and 430 may be driven in the direction generally indicated by arrows 448 in FIG. 4E to eject the specimen 434 from the apparatus 400. This embodiment has the advantage over the embodiment of FIGS. 2A–2C in that feeding and recovery of the specimen 434 is facilitated. The means by which the specimen 434 is held and flexed at the fold line 436, is functionally equivalent to that of the previous embodiments, however.

Figure 5:
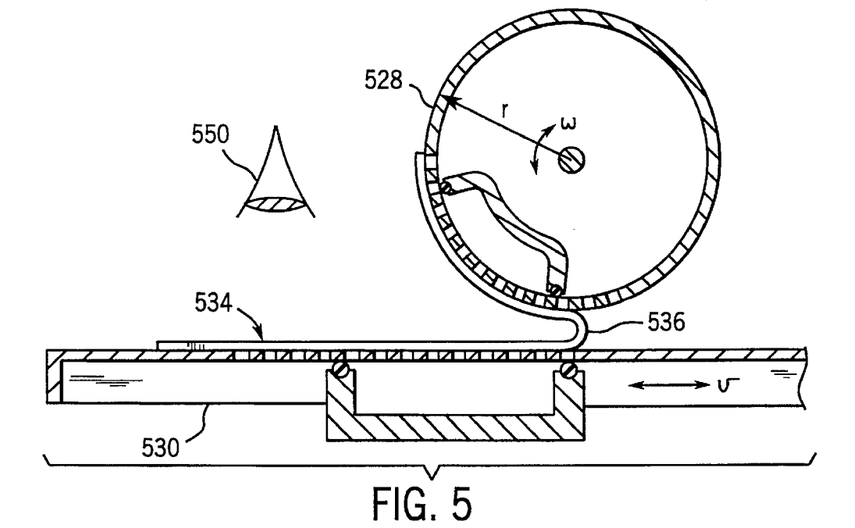
FIG. 5 is a schematic side view of a third alternate embodiment having a sheet secured for testing by a translating plate and rotating drum means in an operational position permitting visual or optical inspection of the specimen during testing.

The use of a translating plate 530 and a cylinder 528 may be combined, as seen in FIG. 5. Such a configuration would allow for visual inspection of the specimen 534 remote from fold 536 by a lens 550 or other optical viewing or analyzing device. In this embodiment, the plate velocity v must equal the speed rω of the surface of cylinder 528 to maintain a constant line of fold 536.

Figure 6:
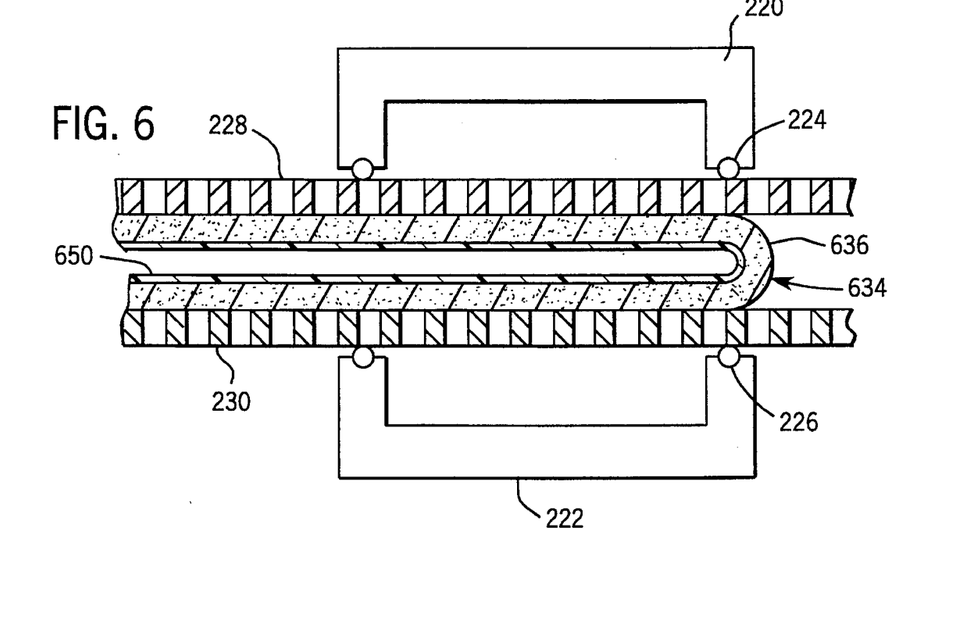
FIG. 6 is a cross sectional side view showing a porous or air permeable sheet secured for testing to a pair of translating plates in an operational position using a thin film to enhance suction to the plates.

The apparatus and methods described thus far presume that the material of which the specimen is composed is sufficiently impermeable to air that a pressure differential can be applied across the specimen to hold it in place for testing. In cases where the specimen is composed of a semipermeable or permeable material, as seen in FIG. 6, a thin, flexible film 650 may be used. Film 650 renders specimen 634 impermeable and creates the holding effect without affecting the rolling fold test. It may be desirable, when inserting the specimen and film, to establish a small gap between the film 650 and the fold 636 of the specimen 634 to avoid undesirable rubbing or other contact between the two materials.

Variations, modifications and other applications of the present invention will become apparent to those presently of ordinary skill in the art after reviewing the specification in connection with the FIGURES. Therefore, the above description of the preferred embodiment is to be interpreted as illustrative rather than limiting. The scope of the present invention is to be limited solely by the scope of the claims which follow.

What is claimed is:

1. A device capable of testing the endurance of a sheet and the endurance and adhesion of surface treatments on the sheet, said device comprising:

a) a first directionally porous surface slidably mounted to a first means for applying a pressure differential to a preselected section of said first surface to hold a preselected portion of a sheet to said first surface;

b) a second directionally porous surface slidably mounted to a second means for applying a pressure differential to a preselected section of said second surface to hold a preselected portion of a sheet to said second surface; wherein a fold is created at a preselected position on a sheet when the sheet is held by said first and second surfaces;

c) means for sliding said first surface relative to said second surface, said sliding means permitting a fold in a sheet held by said first and second surfaces to move over a preselected area of the sheet; and d) means for maintaining a preselected spacing between said surfaces, the spacing of said surfaces determining the radius of a fold in a sheet held by said surfaces.

2. The device of claim 1 wherein said first means for applying a pressure differential to said first surface is a first vacuum box and further wherein said second means for applying a pressure differential to said second surface is a second vacuum box.

3. The device of claim 2 wherein said first surface is a first porous plate connected to said first vacuum box and further wherein said second surface is a second porous plate connected to said second vacuum box.

4. The device of claim 2 wherein said first surface is a preselected portion of a first porous drum connected to said first vacuum box and further wherein said second surface is a preselected portion of a second porous drum connected to said second vacuum box.

5. The device of claim 1 wherein said first surface is a first porous cylinder having a first fixed piston positioned therein, wherein said first cylinder can be oscillated by said sliding means in a preselected direction over a preselected distance;

further wherein said second surface is a second porous cylinder having a second fixed piston positioned therein, wherein said second cylinder can be oscillated by said sliding means in a preselected direction over a preselected distance;

further wherein said first means for applying a pressure differential to a preselected section of said first surface maintains a preselected vacuum within said first cylinder; and further wherein said second means for applying a pressure differential to a preselected section of said second surface maintains a preselected vacuum within said second cylinder.

6. The device of claim 2 wherein said first surface is a first continuous perforated belt connected to said first vacuum box;

further wherein said second surface is a second continuous perforated belt connected to said second vacuum box;

further wherein said means for sliding said first surface relative to said second surface comprises a first pair of rollers for selectively moving said first perforated belt; and further wherein said means for sliding said second surface relative to said second surface further comprises a second pair of rollers for selectively moving said second perforated belt.

7. The device of claim 2 wherein said first surface is a porous plate connected to said first vacuum box and further wherein said second surface is a preselected portion of a porous drum connected to said second vacuum box.

8. The device of claim 3 further comprising mechanical means for securing the ends of a sheet held by said device to said plates.

9. A device capable of testing the endurance of a sheet and the endurance and adhesion of surface treatments on the sheet, said device comprising:
   a) a first directionally porous plate slidably mounted to a first vacuum box;
   b) a second directionally porous plate slidably mounted to a second vacuum box; wherein a fold is created at a preselected position on a sheet when the sheet is held by said first and second plates;
   c) means for sliding said first plate relative to said second plate, said sliding means permitting a fold in a sheet held by said first and second plates to move over a preselected area of the sheet; and
   d) means for maintaining a preselected spacing between said plates, the spacing of said plates determining the radius of a fold in a sheet held by said plates.

10. The device of claim 9 further comprising mechanical means for securing the ends of a sheet held by said device to said plates.

11. A device according to claims 1, 2, 3, 4, 5, 6, 7, 8 or 9 in which the sheet is a currency note.

12. A method capable of testing the endurance of a sheet and the endurance and adhesion of surface treatments on the sheet, said method comprising:
   a) applying a pressure differential to a preselected section of a first slidable directionally porous surface;
   b) applying a pressure differential to a preselected section of a second slidable directionally porous surface;
   c) maintaining a preselected spacing between said surfaces;
   c) securing a portion of a sheet to said first surface;
   d) securing a different portion of said sheet to said second surface, thereby creating a fold at a preselected position on said sheet, the radius of said fold being determined by the spacing between said first and second surfaces; and
   e) selectively sliding said first surface relative to said second surface, thus permitting said fold to move over a preselected area of said sheet.

13. The method of claim 11 wherein the step of selectively sliding said first surface relative to said second surface includes:
   a) controlling the relative velocity of said first and second plates; and
   b) limiting the number of cycles of motion of said first and second surfaces.

14. The method of claim 12 further comprising the step of measuring the wear caused by the preselected movement of said fold over said preselected area of said sheet.

15. The method of claim 11 wherein said sheet is a currency note.

16. The method of claim 12 wherein said sheet is a currency note.

17. The method of claim 13 wherein said sheet is a currency note.

* * * * *